United States Patent
Keenan et al.

[11] Patent Number: 5,900,132
[45] Date of Patent: May 4, 1999

[54] CAPILLARY HOLDER

[75] Inventors: Charles A. Keenan, Irvine; Stephen L. Pentoney, Jr., Yorba Linda; Brian D. Peterson, Ontario; Jack D. McNeal, Long Beach, all of Calif.

[73] Assignee: Beckman Coulter, Inc., Fullerton, Calif.

[21] Appl. No.: 08/671,912

[22] Filed: Jun. 28, 1996

Related U.S. Application Data

[63] Continuation-in-part of application No. 08/518,285, Aug. 23, 1995, Pat. No. 5,635,050, and application No. 08/409,557, Mar. 23, 1995, Pat. No. 5,614,726.

[51] Int. Cl.$^6$ .................... G01N 27/26; G01N 27/447
[52] U.S. Cl. .................... 204/603; 204/451; 204/452; 204/601
[58] Field of Search ................... 204/603, 452, 204/451, 453, 454, 455, 601, 602, 604, 605

[56] References Cited

U.S. PATENT DOCUMENTS

| | | | |
|---|---|---|---|
| 4,985,129 | 1/1991 | Burd | 204/603 |
| 5,274,240 | 12/1993 | Mathies et al. | 204/603 X |
| 5,413,686 | 5/1995 | Klein et al. | 204/603 |
| 5,417,925 | 5/1995 | Goodale et el. | 422/103 |
| 5,516,409 | 5/1996 | Kambara | 204/603 |
| 5,614,726 | 3/1997 | Kaye et al. | 204/603 X |

*Primary Examiner*—William H. Beisner
*Assistant Examiner*—John S. Starsiak, Jr.
*Attorney, Agent, or Firm*—William H. May; P R. Harder; Steven G. Roeder

[57] ABSTRACT

A holder (10) is provided for securing a capillary (30) having a window section (28) including first and second edges (46) (48) to a mount (80). The holder (10) comprises a retaining surface (14) for securing the capillary (30) to the holder (10) and a mounting surface (18) for detachably securing the holder (10) to the mount (80). The retaining surface (14) is attached to the capillary (30) proximate to the opposed first and second edges (46), (48), with a portion of the window section (28) exposed. Since the capillary (30) is secured proximate the opposed first and second edges (46), (48), the fragile capillary window section (28) is protected during manufacturing or installation into an electrophoretic system (32). The retaining surface (14) preferably is sized and shaped to retain a plurality of capillaries (30) to allow for the substantially simultaneous testing of multiple capillaries (30). Optimally, the mounting surface (18) secures the holder (10) to the mount (80) with the capillaries (30) in fluid communication with a support medium supply (106) so that the support medium inside each capillary (30) can be replaced without removing each capillary (30) from the mount (80).

31 Claims, 4 Drawing Sheets

CAPILLARY HOLDER

This application is a continuation-in-part of application Ser. No. 08/518,285 now U.S. Pat. No. 5,635,050 entitled "Electrophoretic System Including Means For Replacing Separation Medium" filed Aug. 23, 1995, by Pentoney, Jr., et al. which is currently pending. The content of U.S. Application Ser. No. 08/518,285 is incorporated herein by reference.

This application is a continuation-in-part of Ser. No. 08/409,557 now U.S. Pat. No. 5,614,726, filed on Mar. 23, 1995, and issued to Kaye et al on Mar. 25, 1997.

BACKGROUND

1. Field of the Invention

The present invention relates to capillary holders useful in capillary electrophoresis instruments. More particularly, the present invention involves holders which secure and protect capillaries during their installation and subsequent use in electrophoretic separation.

2. Description of Related Art

A detailed description of capillary electrophoresis is provided in U.S. Pat. No. 4,675,300 issued to Zare et al. and U.S. Pat. No. 5,484,571, issued to Pentoney, Jr. et al., both of which are incorporated herein by reference.

Capillary electrophoresis is commonly used in analytical and biomedical research for the rapid separation and analysis of charged species including synthetic polynucleotides, DNA sequencing fragments, DNA restriction fragments, amino acids, optical isomers of dansyl amino acids, and the separation of proteins, viruses and bacteria.

Capillary electrophoresis typically utilizes an electrokinetic differential to separate and transport components of a sample inside a capillary. A variety of detectors are available for detecting the sample components including uv-visible detection, electrochemical detection and more recently laser induced fluorescence detection which involves labeling sample components with a fluorescent tag, such as, e.g., fluorescein.

Laser induced fluorescence utilizes one or more lasers to illuminate a window section of the capillary. This illumination results in the laser excitation of fluorescent material within the window section and causes the fluorescent material to emit radiation. These emission are collected by a collection device and sent to a detector which converts the emission energy to a usable signal for analysis. Many capillary systems will accommodate multiple fluorescent labels each of which has its own emission characteristic or emission wavelength. Accordingly, information about the nature of many sample components can be obtained by collecting the fluorescent emissions from the components and noting the wavelength and/or intensity of the emission.

In order to increase sample throughput, recent capillary electrophoresis system designs incorporate multiple capillaries in a single system. Many of these systems use only a single detector to interrogate and detect sample components in multiple capillaries. In order to handle and install multiple capillaries, great care must be taken to protect the capillaries and guide them into position. Moreover, since it is desirable to collect as much of the fluorescent emissions as possible to maximize the detection sensitivity, proper alignment between a laser or the radiation source, each capillary window section, and the fluorescent emissions collector is critical. When multiple capillary systems are utilized, installing the capillaries and properly aligning each capillary window can be very challenging.

Typical capillaries are in a tubular configuration having a wall thickness of between 25–500 microns. The wall is made of glass, fused silica or an organic material such as polytetrafluoroethylene, commonly sold under the trademark "Teflon" by DuPont. In order to protect fused silica capillaries the wall is strengthened with a polyimide coating. However, the polyimide coating is removed from the capillary window section to allow light to pass. resulting in a relatively weak and fragile capillary window section. Thus a major consideration in installing and removing capillaries is to avoid damaging the window and breaking the capillaries.

The concern for protecting and securing capillaries is especially critical for high volume users. Although capillaries have long useful lives, they are not indefinite and they need to be removed and replaced. The primary reason for replacing capillaries is the degradation and the loss of interior wall coatings which are introduced on the walls to reduce or eliminate electroosmotic flow during the electrophoretic process. Moreover, many electrophoretic separations require that the separation medium be pumped from each capillary and replaced by pumping in fresh medium after each separation. Thus, the capillaries need to be secured during the separation medium replacement process and they need to be protected when they are replaced and aligned.

One way of retaining a single capillary is provided in U.S. Pat. No. 5,484,571. With reference to FIG. 4 of U.S. Pat. No. 5,484,571, the capillary can be inserted through and retained by small holes in the sides of a parabolic reflector. However, this system is not entirely satisfactory since the fragile capillary window section is not protected during the capillary coating process or its installation into the parabolic reflector. Additionally, in this system the window section can be difficult to position properly in front of the focal spot of the light source and it holds only one capillary.

Accordingly, there is a need for a device that supports the window section of the capillary during its installation into an electrophoretic system, and that facilitates the correct alignment between the window section and the focal spot of the light source. Further, there is a need for a device which retains a plurality of capillaries and allows for the replacement of the support medium within the capillary without removing the capillary from the electrophoretic system.

SUMMARY

The present invention is directed to a capillary holder that satisfies these needs. A capillary holder having features of the present invention includes a retaining surface for securing a capillary to the holder and a mounting surface. The capillary includes a window section having opposed first and second edges. The retaining surface secures the capillary proximate to the first and second edges to protect the window section. The mounting surface detachably secures the holder to a mount with the capillary window section protected by the retaining surface.

As described in detail below, the capillary holder is capable of (i) supporting the window section during manufacturing and installation into an electrophoretic system, (ii) maintaining the window section in correct alignment with a focal spot of an electrophoretic system, (iii) securely retaining a plurality of capillaries, and (iv) allowing for support medium replacement without removing the capillary or capillaries from the electrophoretic system.

The retaining surface can include a plurality of holder tabs extending forwardly from a front surface of a holder body.

Typically, each capillary is secured to a first holder tab proximate the first edge of the window section and a second holder tab proximate the second edge of the window section to support the window section. An adhesive can be used for fixedly securing each capillary to the holder tabs.

Preferably, the retaining surface is sized to retain a plurality of capillaries with a portion of each window section of each capillary exposed. This allows for substantially simultaneous testing of a sample solution in a number of capillaries, thereby increasing the system throughput.

The mounting surface can be a tubular member sized and shaped to fit within a mount aperture of the mount. Further, the holder can include a holder stop retaining the window section(s) at the proper height above the mount and an alignment member aligning the capillary or capillaries relative to the focal spot. Since the distance between the holder stop and the window section is fixed and the alignment member maintains alignment of the holder, the holder can be attached to a manufacturing stand for precisely manufacturing the window section and subsequently installed in correct alignment with the focal spot in the electrophoretic system.

Optimally, the mounting surface secures the holder to the mount with the capillary or capillaries in fluid communication with a support medium supply so that the support medium in the capillary or capillaries can be replaced without removing the capillaries from the system. This can be accomplished by using (i) a capillary seal for sealing an interface formed between an external surface of the capillary and the mounting surface and (ii) a holder seal for sealing an interface formed between the mounting surface and the support medium supply.

Thus, the present invention provides a holder which supports the window section of the capillary during manufacturing and installation into the electrophoretic system and contributes to maintaining the correct alignment between the window section and the focal spot of the light source. Further, the holder is capable of retaining a plurality of capillaries and allowing for sample replacement within the capillaries without removing the capillaries from the electrophoretic system.

BRIEF DESCRIPTION OF THE DRAWINGS

These and other features, aspects and advantages of the present invention will become better understood with reference to the following description, appended claims and accompanying drawings where:

DESCRIPTION OF THE INVENTION

With reference to the Figures, a holder 10 according to the present invention comprises (i) a holder body 12; (ii) a retaining surface 14; (iii) an adhesive 16; (iv) a mounting surface 18; (v) a holder stop 20; (vi) an alignment member 22; (vii) a capillary seal 24; and (viii) a holder seal 26.

The holder 10 is useful in any application which requires a window section 28 of a capillary 30 or multiple capillaries to be accurately positioned and secured during manufacturing or installation into an electrophoretic system 32. The present invention is also useful for alternate capillary detection systems (not shown) including UV and visible detection.

Each capillary 30 comprises a tubular wall 34 having opposed, open, first and second ends 36, 38. Each capillary 30 has an inside diameter 40 of between 5 to 500 microns and typically less than 200 microns. The wall 34 of the capillary 30 is made of glass, fused silica or an organic material such as polytetrafluorethyelene, commonly sold under the trademark "Teflon" by DuPont. An external surface 44 of the wall 34 of each capillary includes a polyimide coating to strengthen the wall 34. The window section 28 is the area which is illuminated by a light source (not shown) during testing and is not covered by the polyimide coating. The window section 28 includes opposed, first and second edges 46, 48.

The capillary 30 is filled with a sample solution (not shown) comprising of a separation support medium (not shown) such as an electrolyte solution, gel electrolyte or other suitable conductive medium and the sample (not shown) to be electrophoretically separated. The sample can be injected into the capillary 30 by any number of conventional technologies.

Figures 1, 4, 5:
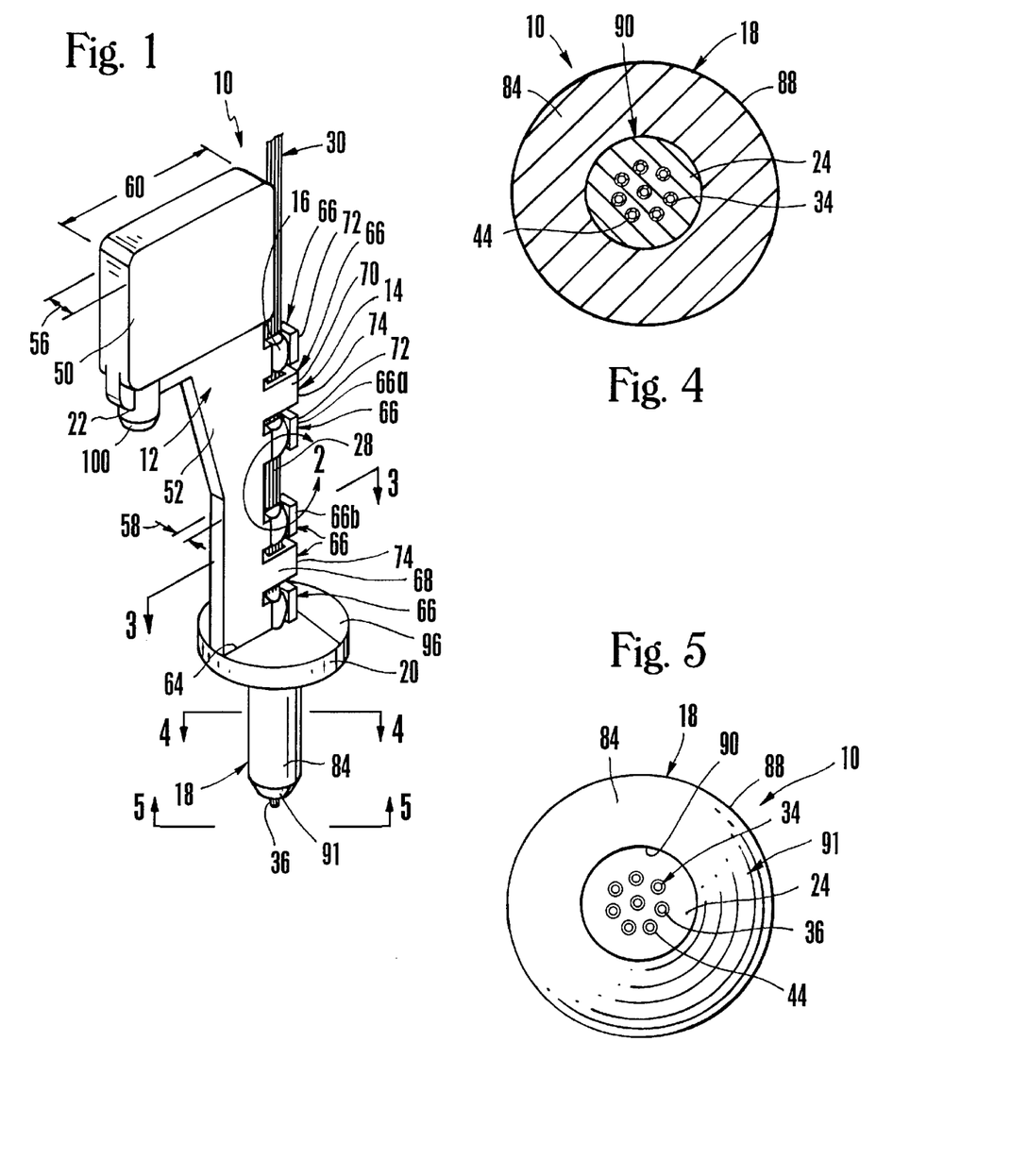
FIG. 1 is a perspective view of a holder having features of the present invention and a plurality of capillaries.
FIG. 4 is a cutaway view taken from line 4—4 in FIG. 1.
FIG. 5 is a bottom plan view of the holder of FIG. 1.
Figure 3:
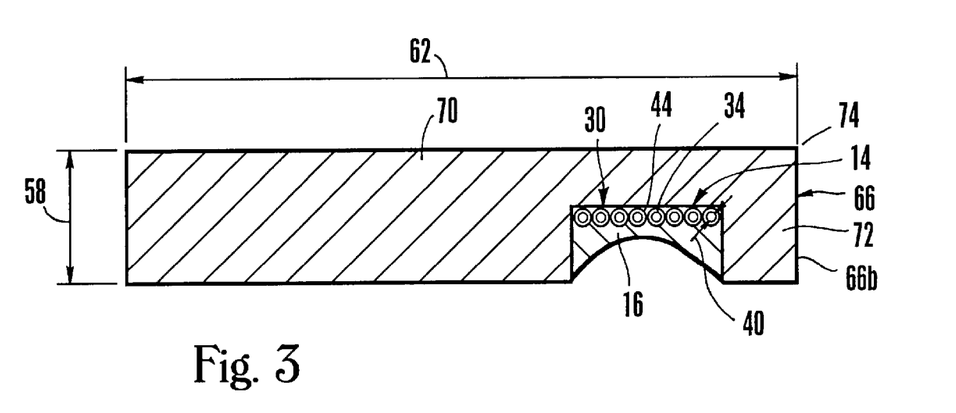
FIG. 3 is a cutaway view taken from line 3—3 in FIG. 1.

Referring to FIG. 1, the holder body 12 connects the retaining surface 14 to the mounting surface 18, the holder stop 20 and the alignment member 22. The design of the holder body 12 varies according to the design of the electrophoretic system 32. In the embodiment shown in the Figures, the holder body 12 is "key" shaped having a thin, rectangular upper section 50 and a thinner, rectangular strip 52 extending downwardly from the upper section 50. The holder body 12 shown in FIG. 1, is about one and five-eighths (1⅝) inches long. Referring to FIGS. 1 and 3, the upper section 50 has a thickness 56 of about one-eighth (⅛) of an inch while the strip 52 has a thickness 58 of about one-sixteenth (1/16) of an inch. The upper section 50 has a width 60 of about nine-sixteenths (9/16) of an inch, while the strip 52 has a width 62 which varies from about one-quarter (¼) of an inch proximate the upper section 50 to about one-eighth (⅛) near a bottom end 64 of the holder body 12.

The retaining surface 14 retains the capillaries 30 to the holder 10 with at least a portion of the window section 28 exposed. Preferably, substantially the entire window section 28 is exposed to allow for maximum sensitivity of the electrophoretic system 32.

As shown in FIG. 1, the retaining surface 14 can comprise a plurality of holder tabs 66 extending from a front surface 68 of the holder body 12. The holder tabs 66 are sized and shaped to receive one or more capillaries 30 and the size varies according to the number of capillaries 30 retained by the holder 10.

In the embodiment shown in the figures, the holder tabs 66 are sized to securely retain eight capillaries 30 in a side-by-side, substantially coplanar position and each holder tab 66 includes a body section 70 extending forwardly from the front surface 68 about one-sixteenth (1/16) of an inch and a lip section 72 extending transversely from a proximal end 74 of the body section 70 about one-thirty-second (1/32) of an inch.

Figure 2:
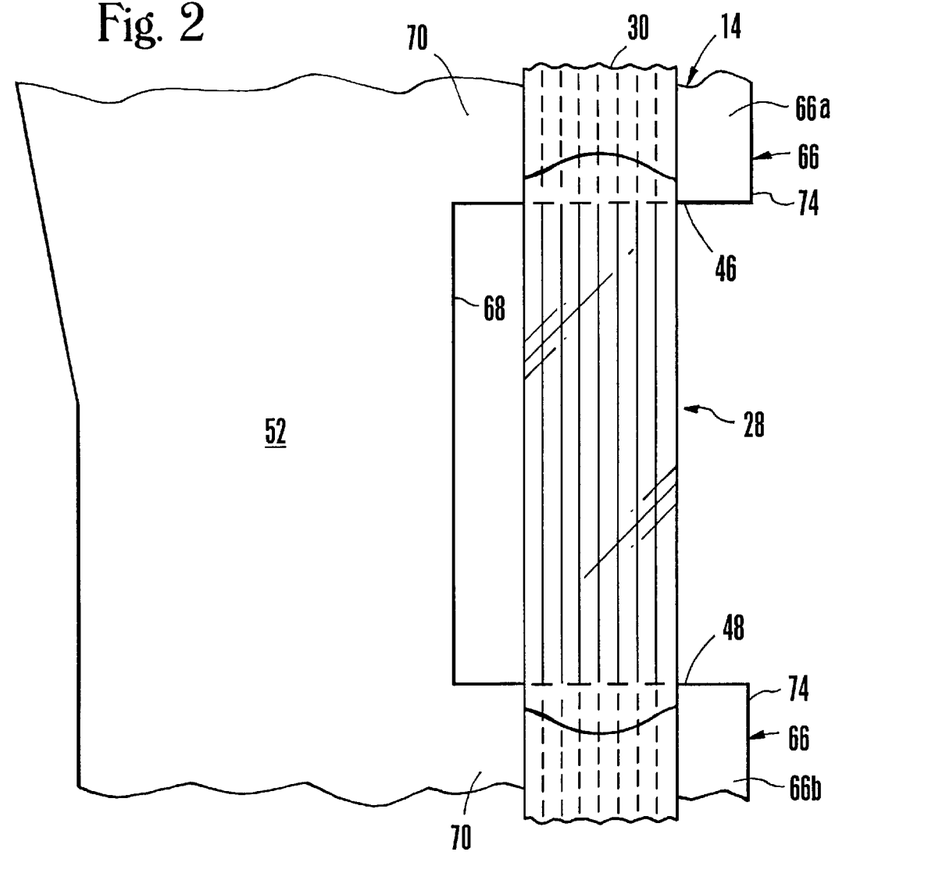
FIG. 2 is an exploded view taken at line 2 in FIG. 1.

Referring to FIG. 2, at least a first holder tab 66a is attached proximate to the first edge 46 of the window section and a second holder tab 66b is attached proximate the second edge 48 of the window section 28. The first and second holder tabs 66a, 66b securely retain the window section 28 and protect it from breaking during manufacturing and installation.

The embodiment shown in FIGS. 1 and 6 includes three holder tabs 66 above the window section 28 and three holder tabs 66 below the window section to secure the window section 28. The lip sections 72 of the first and second holder tabs 66a, 66b face the same direction. The lip sections 72 of the two holder tabs 66 above the first holder tab 66a face opposite directions and the lip section 72 to the two holder tabs 66 below the second holder tab 66b face opposite directions to facilitate easy installation of the capillaries 30 onto the holder 10, to facilitate molding and retention of the capillaries 30. Alternately, the number and shape of the holder tabs 66 can vary according to the design of the electrophoretic system.

An adhesive 16 such as a thermoset epoxy or the quick set epoxy sold under the tradename Trubond available at most hardware stores can be used to fixedly secure the capillaries 30 to the retaining surface 14. Alternatively, any adhesive with relatively quick setting time and good adhesive strength or an adhesive used with double sided tape can be used to secure the capillaries 30 to the retaining surface 14. The adhesive 16 must not adversely react with the retaining surface 14 or capillaries 30.

Figure 6:
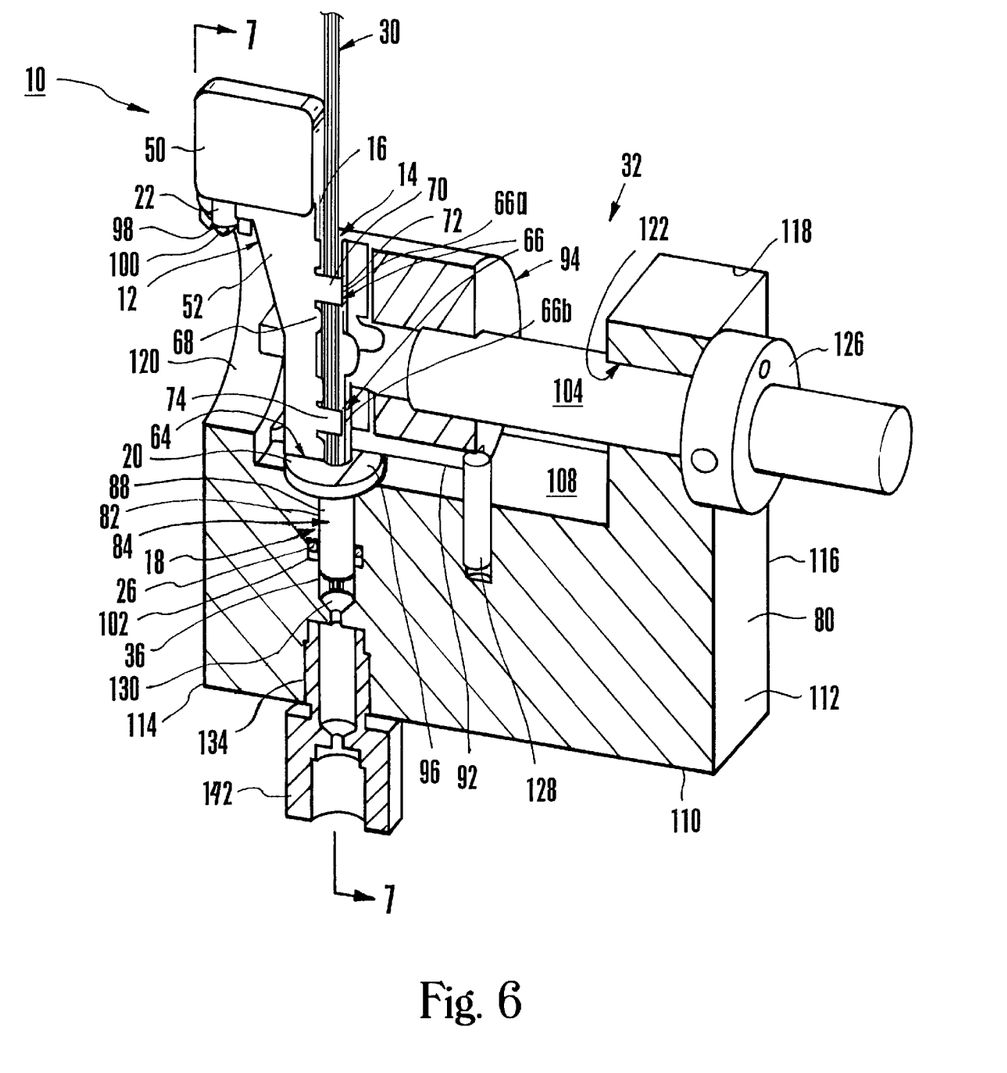
FIG. 6 is a perspective view of the holder of FIG. 1 and a portion of an electrophoretic system in partial cutaway.

Referring to FIG. 6, the mounting surface 18 retains the holder 10 to a mount 80. The size and shape of the mounting surface 18 varies according to the design of the mount 80 and the number of capillaries 30 to be retained. The mount 80 includes a mount aperture 82 having a circular cross-section and the mounting surface 18 includes a tubular member 84 which extends downwardly from the bottom end 64 of the holder body 12. The mount aperture 82 defines an interior surface of the mount 80. An outer surface 88 of the tubular member 84 is sized to fit within the mount aperture 82 and an inner surface 90 of tubular member 84 is sized to receive the plurality of capillaries 30.

In the embodiment shown in the Figures, the tubular member 84 is approximately one-half (½) inches long, the outer surface 88 has a diameter of about one-eighth (⅛) of an inch and the inner surface 90 has a diameter of about one-sixteenth (1/16) of an inch. The tubular member 84 includes a tapered proximal end 91 to facilitate insertion of the tubular member 84 into the mount aperture 82.

As shown in FIGS. 1, 4 and 5, the first ends 36 of the capillaries extend into the tubular member 84 to facilitate replacement of the support medium inside the capillaries 30. Preferably, the first ends 36 of the capillaries 30 extend through and below the tubular member 84 for ease of installation of the capillary seal 24.

The holder stop 20 retains the tubular member 84 in the mount aperture 82. The holder stop 20 can be implemented in a number of alternate ways. For example, in the embodiment shown in the Figures, the holder stop 20 is a disk-shaped projection positioned between the holder body 12 and the tubular member 84. The disk-shaped projection has a diameter larger than the diameter of the mount aperture 82 so that the holder stop 20 does not slide into the mount aperture 82.

With reference to FIG. 6, an exterior surface 92 of a parabolic reflector 94 slides over and contacts the holder stop 20 to retain the tubular member 84 in the mount aperture 82. The holder stop 20 can include a forwardly facing, wedge-shaped lip 96 to facilitate the sliding engagement between the parabolic reflector 94 and the holder stop 20. Alternately, a bolt (not shown) which extends through the holder stop 20 and threads into the mount 80 could be used to prevent the holder 10 from moving vertically.

With the capillaries 30 secured to the retaining surface 14, the distance between the holder stop 20 and the window section 28 is held constant. Thus, the holder can be secured to a manufacturing stand (not shown) which removes the polyimide coating from the capillary 30 to create the window section 28 in the correct location. Subsequently, the window section 28 will be at the proper height in front of a focal spot (not shown) of the light source when the holder 10 is installed in the electrophoretic system 32.

The alignment member 22 insures that the holder 10 and the capillaries 30 are properly aligned with the focal spot by preventing the holder 10 from rotating relative to the mount 80. The alignment member 22 can also be implemented in a number of alternate ways. For example, in the embodiment shown in the Figures, the alignment member 22 is a right, cylindrical-shaped projection extending downwardly from the upper section 50 of the holder body. The projection is sized and shaped to fit within an upper aperture 98 of the mount 80. The alignment member 22 inserted into the upper aperture 98 prevents the holder 10 from rotating relative to the mount 80 and therefore maintains the capillaries 30 in proper alignment with the focal spot of the light source. The alignment member 22 can include a tapered end 100 which facilitates insertion into the upper aperture 98.

The holder 10, including the holder body 12, retaining surface 14, mounting surface 18, holder stop 20 and alignment member 22 are preferably manufactured as an integral unit for ease in manufacturing. The holder 10 can be molded from a hard plastic such as polyphenylene sulfide (PPS) or alternate materials such as acrylonitrile butadiene styrene (ABS).

Referring to FIGS. 4 and 5, the capillary seal 24 seals an interface formed between the inner surface 90 of the tubular member and the external surface 44 of the capillaries. The capillary seal 24 must not be affected by the sample and the support medium and must not adversely affect the sample and the support medium. The capillary seal 24 can be an adhesive disposed in the inner surface 88 which is not adversely affected by the sample solution. An adhesive such as the aforementioned Trubond makes is a suitable seal. The first ends 36 of the capillaries are not enclosed by the capillary seal 24.

The holder seal 26 seals an interface formed between the outer surface 88 of the tubular 84 and the interior surface of the mount aperture 82. With reference to FIG. 6, the holder seal 26 can be an O-ring type seal which fits in a groove 102 in the interior surface of the mount aperture 82 to seal the outer surface 88 of the tubular member 84 and the interior surface of the mount aperture 82. The O-ring type seal can be made of buna-n or some other material which is not adversely affected and does not adversely affect the sample solution.

The holder 10 secures the capillary or capillaries 30 to the mount 80. The mount 80 can be part of a manufacturing stand (not shown) for manufacturing the capillaries 30. During manufacturing, after the capillaries 30 are coated with the polyimide coating, the capillaries 30 can be installed into the holder 10 and the mounting surface 18 attached to the manufacturing stand. Subsequently, a laser (not shown) can be used to make the window section 28 by removing the polyimide coating. Since the position of the capillary 30 is fixed in the holder 10, the distance between the holder stop 20 and the window section 28 is fixed so that the window section 28 is precisely cut into the capillary 30.

Figure 7:
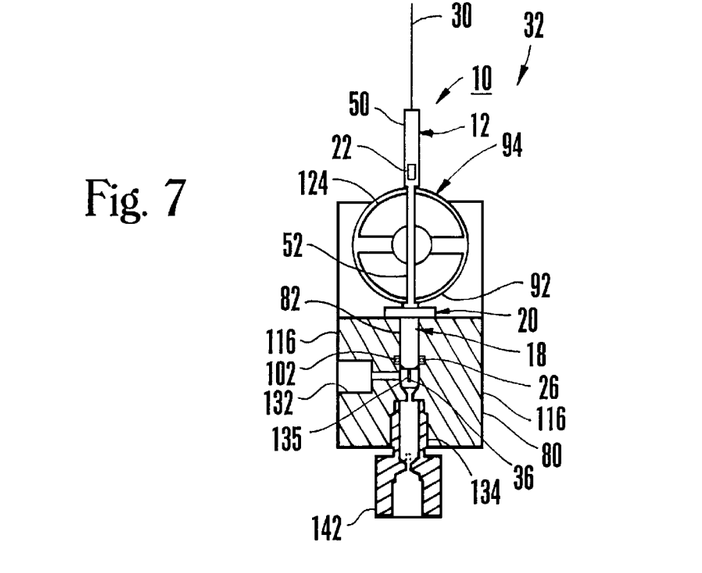
FIG. 7 is a cutaway view taken from line 7—7 in FIG. 6.
Figure 8:
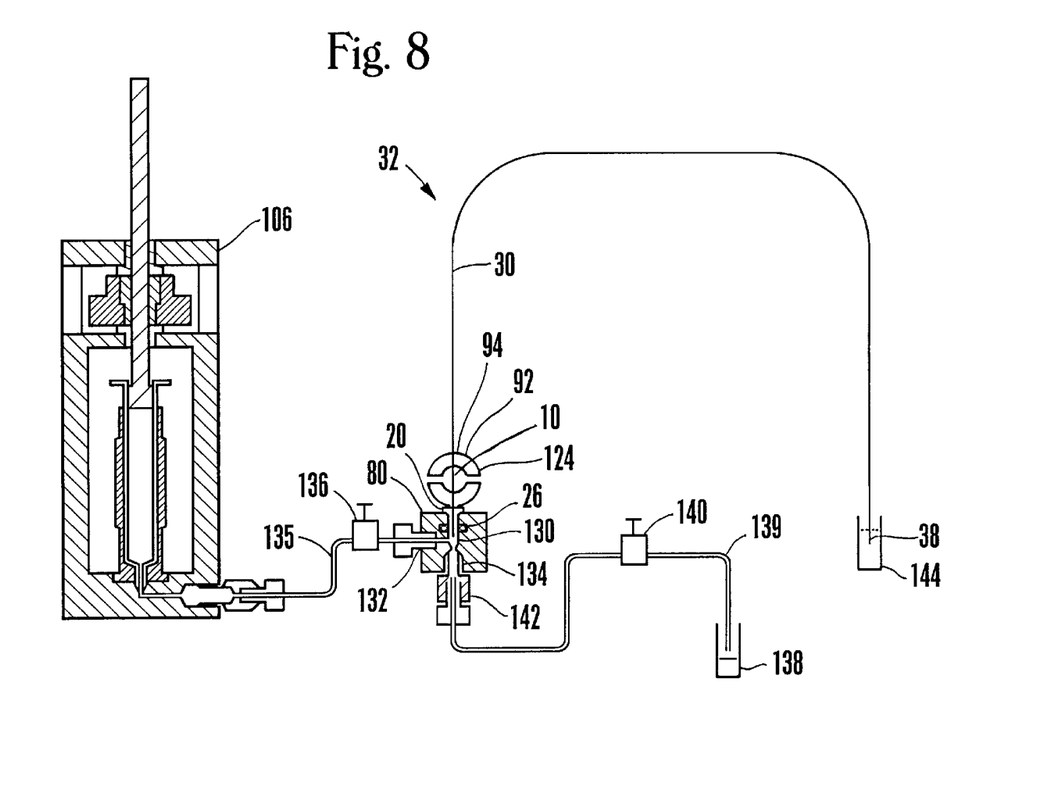
FIG. 8 is a schematic view of a portion of an electrophoretic system having features of the present invention.

Alternately, the mount 80 is part of the electrophoretic system 32, the design of which can vary. Referring to FIGS. 6, 7 and 8, the components of electrophoretic system 32 shown in the Figures includes the mount 80, the parabolic reflector 94, the holder 10, the plurality of capillaries 30, a reflector guide 104 and a support medium supply 106. A light source for emitting a beam of light, a collector for collecting the beam of light, lenses for focusing the light from the light source and other components of the electrophoretic system are not included to simplify the Figures.

In the embodiment shown in FIGS. 6 and 7, the mount 80 is rectangular having a top surface 108, a bottom surface 110, a front surface 112, a rear surface 114 and opposed side surfaces 116. A rectangular, front projection 118 extends upwardly from the top surface 108 proximate the front surface 112 and a rectangular, rear projection 120 extends upwardly from the top surface 108 proximate the rear surface 114. The front projection 118 includes a guide aperture 122 extending therethrough to sliding receive the reflector guide 104. The rear projection 120 includes the upper aperture 98 to receive and retain the alignment member 22.

The parabolic reflector 94 is secured to the reflector guide 104. The reflector guide 104 and the parabolic reflector 94 attached thereto slide relative to the mount 80 to facilitate installation of the holder 10 to the mount 80. A guide stop 126 stops the reflector guide 104 from sliding too far and a guide pin 128 prevents the parabolic reflector 94 from rotating. Further, a front surface 124 of the parabolic reflector 94 can include a pair of opposed slots (not shown) to receive the capillaries 30.

In the embodiment shown in FIG. 6, installation of the holder 10 to the mount 80 requires that the parabolic reflector 94 and the reflector guide 104 moved away from the rear projection 120. Next, the tubular member 84 is inserted into the mount aperture 82 with the alignment member 22 aligned with the upper aperture 98. Subsequently, the parabolic reflector 94 and the reflector guide 104 are moved back towards the rear projection 120. The parabolic reflector 94 retains the holder 10 to the mount 80.

As previously mentioned, the holder 10 allows for support medium replacement without removing the capillary 30 from the mount 80. An electrophoretic system providing for support medium replacement and useful with the prevent invention is described in detail in U.S. application Ser. No. 08/518,285 (Beckman No. 129D-1276). As provided in U.S. application Ser. No. 08/518,285, to facilitate the replacement process, the mount 80 includes a manifold 130 in fluid communication with an inlet port 132, an outlet port 134, and the mount aperture 82.

Referring to FIGS. 6, 7 and 8, the inlet port 132 is connected in fluid communication with the support medium supply 106 using conventional tubing 135. The support medium supply 106 can be a pump or syringe which delivers a new support medium for testing. Alternatively, the support medium supply 106 can be a programmable delivery system (not shown). A first valve 136 is positioned between the inlet port 132 and the support medium supply 106.

The outlet port 134 is connected in fluid communication with a waste reservoir 138 using conventional tubing 139. A second valve 140 is positioned between the outlet port 134 and the waste reservoir 138. Also, an electrode fitting 142 is threaded into the outlet port 134. The electrode fitting 142 is used as one terminal for applying the electrical potential.

With reference to FIGS. 6, 7 and 8, the tubular member 84 fits into the mount aperture 82 with the first end 36 of the capillaries extending into and in to fluid communication with the manifold 130. The capillary seal 24 and the holder seal 26 seal the interface between the first end 36 of the capillaries 30 and the manifold 130. The second end 38 of the capillary is disposed in a run buffer 144.

With reference to FIG. 8, support medium replacement in the capillaries 30 can be accomplished with the following three steps. After each capillary 30 is purged of the old support medium, the second valve 140 is opened and the old support medium from the manifold 130 is purged into the waste reservoir 138. With the first valve 136 open and the second valve 140 closed, fresh support medium is delivered through the inlet port 132 to the manifold 130 from the support medium supply 106. The fresh support medium passes through the first valve 136 and enters the first end 36 of each capillary. The fresh support medium pushes the old support medium out the second end 38 of each capillary into the run buffer 144.

Subsequently, after refilling the capillaries, the first valve 136 is closed and the second valve 140 remains open. The system is now ready for testing with the fresh support medium.

In operation, a high electrical potential is applied by a power supply (not shown) between the electrode fitting 142 and the run buffer 144. The sample solution in the manifold 130 completes the electrical circuit between the electrode fitting 142 and the first end 36 of the capillaries. The electrical potential causes the sample in the capillary or capillaries to be separated into its components. As the sample components migrate from the first end 36 of each capillary towards the second end 38 of each capillary, the sample components pass the window section 28. The light source is used to induce fluorescence of the separated components of the sample and such fluorescence is then detected by the collector for detection in a manner known to those skilled in the art.

The operation of a multiple capillary electrophoretic system is provided in U.S. application Ser. No. 08/429,406 by S. Pentoney et al. filed Apr. 26, 1995 (Beckman No. 45D-1324) and entitled "A Multicapillary Fluorescent Detection System", which is incorporated herein by reference.

The holder 10 provided herein has many advantages over the prior art holders, including supporting the window section 28 during manufacturing and installation into an electrophoretic system, maintaining the window section 28 in correct alignment in the electrophoretic system, securely retaining a plurality of capillaries, and allowing for separation support medium replacement without removing the capillaries from the electrophoretic system.

While the present invention has been described in considerable detail with reference to certain preferred versions, other versions are possible. For example, the alignment member 22 can comprise a projection (not shown) extending vertically on the outer surface 88 of the tubular member 84 and a corresponding groove (not shown) in the interior surface of the mount aperture 82. Therefore, the spirit and scope of the appended claims should not be limited to the description of the preferred versions contained herein.

What is claimed is:

1. A holder for detachably securing a capillary to a capillary electrophoresis system, the capillary including a window section, the window section having opposed first and second edges, the holder comprising:

a holder body;

a first holder tab secured to the holder body, the first holder tab being adapted to attach to the capillary proximate to the window section, the first holder tab cantilevering outward from the holder body;

means for attaching the capillary to the first holder tab; and a mounting means secured to the holder body, the mounting means being adapted to selectively attach to the capillary electrophoresis system to detachably secure the holder body, the first holder tab, and the capillary to the capillary electrophoresis system.

2. The holder of claim 1 further comprising a second holder tab, the second holder tab cantilevering outwardly from the holder body, the first holder tab and second holder tab being spaced apart sufficiently so that the first holder tab is adapted to retain the capillary proximate the first edge of the window section and the second holder tab is adapted to retain the capillary proximate the second edge of the window section.

3. A capillary assembly for use with a capillary electrophoresis system, the capillary assembly comprising (i) the holder of claim 1, (ii) a capillary having a substantially tubular shaped window section and (iii) wherein the means for attaching includes a retainer adhesive directly securing the capillary to the first holder tab.

4. The capillary assembly of claim 3 wherein the mounting means comprises a tubular member extending away from the holder body, wherein the capillary is secured to the first holder tab with a portion the capillary extending into the tubular member, and wherein the holder further comprises a sealing adhesive for sealing an interface formed between an eternal surface of the capillary and the tubular member.

5. A capillary assembly for use with a capillary electrophoresis system, the capillary assembly comprising (i) the holder of claim 1 and (ii) a plurality of spaced apart capillaries attached to the first holder tab.

6. A capillary electrophoresis system comprising:

a mount;

the holder of claim 1 with the mounting, means detachably secured to the mount; and a capillary secured to the first holder tab, the capillary including a substantially tubular shaped window section.

7. The capillary electrophoresis system of claim 6 further comprising a reflector which surrounds a portion of the window section of the capillary.

8. The capillary electrophoresis system of claim 6 further comprising a support medium supply in fluid communication with the capillary, the support medium supply being adapted to supply support medium to the capillary to fill the capillary with the support medium.

9. A holder for detachably securing a plurality of capillaries to a capillary electrophoresis system, each capillary including a window section, the holder comprising:

a holder body;

a retaining means secured to the holder body, the retaining means being adapted to attach to each capillary proximate to the window section of each capillary, the retaining means being positioned outward from the holder body;

means for attaching the capillary to the retaining means; and a mounting means secured to the holder body, the mounting means being adapted to selectively attach to the capillary electrophoresis system to detachably secure the holder body, the retaining means, and the plurality of capillaries to the capillary electrophoresis system.

10. The holder of claim 9 wherein the retaining means includes a first holder tab which cantilevers outwardly from the holder body.

11. A capillary assembly for use with a capillary electrophoresis system, the capillary assembly comprising (i) the holder of claim 10, (ii) a plurality of capillaries, each capillary including a tubular shaped window section, each window section including a first edge and a second edge, and (iii) wherein the means for attaching comprises a retainer adhesive fixedly securing the plurality of capillaries to the first holder tab with the window section of each capillary substantially side by side and substantially coplanar.

12. The capillary assembly of claim 11 wherein the retainer means further comprises a second holder tab, the second holder tab cantilevering outwardly from the holder body, the first holder tab and second holder tab being spaced apart sufficiently so that the first holder tab retains each of the capillaries proximate the first edge of each window section and the second holder tab retains each of the capillaries proximate the second edge of each window section.

13. The capillary assembly of claim 11 wherein the mounting means includes a tubular member extending away from the holder body, wherein each of the capillaries is secured to the first holder tab with at least a portion each capillary extending into the tubular member, and wherein the holder includes a sealing adhesive for sealing an interface formed between an external surface of each of the capillaries and the tubular member.

14. A capillary electrophoresis system comprising:

a mount; and the capillary assembly of claim 11 having the mounting means detachably secured to the mount.

15. The capillary electrophoresis system of claim 14 further comprising a reflector which surrounds a portion of each window section of each capillary.

16. The capillary electrophoresis system of claim 14 further comprising a support medium supply in fluid communication each of the capillaries, the support medium supply being adapted to supply support medium to each of the capillaries to fill each capillary with the support medium.

17. A capillary assembly which is adapted to be secured to a capillary electrophoresis system, the capillary electrophoresis system including a support medium supply, the support medium supply being adapted to provide a pressurized supply of a support medium, the capillary assembly comprising:

a first capillary including an open first end, the first capillary also including a window section having a first edge and a second edge;

a holder comprising (i) a holder body, (ii) a first holder tab and a second holder tab secured to the holder body, each holder tab cantilevering outwardly away from the holder body, the first holder tab and second holder tab being spaced apart sufficiently so that the first holder tab retains the first capillary proximate the first edge of the window section and the second holder tab retains the first capillary proximate the second edge of the window section and (iii) a mounting means secured to the holder body, the mounting means being adapted to attach to the capillary electrophoresis system to secure the holder body, the first and second holder tabs and the first capillary to the capillary electrophoresis system with the first end of the first capillary in fluid communication with the support medium supply so that the first capillary is adapted to be filled with support medium from the support medium supply; and means for attaching the capillary to the first holder tab and the second holder tab.

18. The capillary assembly of claim 17 wherein the first and second holder tabs are positioned outward from the holder body so that a substantially tubular shaped window section of the first capillary is positioned outward from the holder body.

19. The capillary assembly of claim 17 wherein the mounting means is adapted to be detachably secured to the capillary electrophoresis system to selectively secure the holder body, the first and second holder tabs and the first capillary to the capillary electrophoresis system.

20. The capillary assembly of claim 17 wherein the means for attaching comprises a retainer adhesive directly securing the first capillary to the holder tabs.

21. The capillary assembly of claim 17 wherein the mounting means includes a tubular member extending away from the holder body, wherein the first capillary is secured to the holder tabs with at least a portion of the first capillary extending into the tubular member, and wherein the holder further comprises a sealing adhesive for sealing an interface formed between an external surface of the first capillary and the tubular member.

22. The capillary assembly of claim 17 including a second capillary secured to the holder tabs, the second capillary including a first end in fluid communication with the support medium supply so that the second capillary is adapted to be filled with the support medium from the support medium supply.

23. A capillary electrophoresis system comprising:

a mount;

the capillary assembly of claim 17 having the mounting means secured to the mount; and a support medium supply in fluid communication with the first end of the first capillary.

24. The capillary electrophoresis system of claim 23 further comprising a reflector which surrounds portion of the window section of the first capillary.

25. A method for manufacturing a capillary assembly, the capillary assembly being adapted to be used with a capillary elecrophoresis system, the method comprising the steps of:

providing a first capillary;

providing a holder for the capillary, the holder including (i) a holder body; (ii) a first holder tab which cantilevers and extends away from the holder body; (iii) a second holder tab which cantilevers and extends away from the holder body; and (iv) a mounting means secured to the holder body, the mounting means being adapted to selectively attach to the capillary electrophoresis system to detachably secure the holder to the capillary electrophoresis system; and securing the first capillary to the first holder tab and the second holder tab with the first capillary positioned outwardly from the holder body.

26. The method of claim 25 further comprising the step of creating a substantially tubular shaped window section in the first capillary, the window section having a first edge and second edge.

27. The method of claim 26 wherein the step of securing the first capillary includes the step of utilizing a retainer adhesive for securing the first capillary to the first holder tab and the second holder tab.

28. The method of claim 26 wherein the step of securing the first capillary includes the steps of securing the first holder tab to the first capillary proximate to the first edge and securing the second holder tab to the first capillary proximate to the second edge.

29. The method of claim 25 further comprising the step of positioning a portion of the capillary within a tubular member, the tubular member being secured to the holder body, and the step of sealing an interface formed between an external surface of the first capillary and the tubular member with a sealing adhesive.

30. The method of claim 25 further comprising the step of providing a second capillary and the step of securing the second capillary to the first holder tab and the second holder tab.

31. The method of claim 25 further comprising the step of creating a substantially tubular shaped window section in the first capillary, the step of providing a second capillary having a substantially tubular shaped window section and the step of securing the second capillary to the first holder tab and the second holder tab with the window section of the second capillary adjacent and substantially coplanar with the window section of the first capillary.

* * * * *